United States Patent [19]

Mathew

[11] Patent Number: 4,498,903
[45] Date of Patent: Feb. 12, 1985

[54] INTERORAL TUBE FIXING DEVICE

[76] Inventor: Christina C. Mathew, 1600 Hagy's Ford Rd. 2-0, Narberth, Pa. 19072

[21] Appl. No.: 437,614

[22] Filed: Dec. 21, 1982

[51] Int. Cl.³ .............................................. A61M 16/00
[52] U.S. Cl. ........................... 604/174; 128/DIG. 26; 604/179
[58] Field of Search ............... 604/174, 179, 177, 180, 604/54; 128/DIG. 26, 136, 346

[56] References Cited

U.S. PATENT DOCUMENTS

| 3,107,667 | 10/1963 | Moore | 128/136 |
| 3,522,805 | 8/1970 | Wallshein | 128/136 |
| 3,993,081 | 11/1976 | Cussell | 128/DIG. 26 |
| 4,275,725 | 6/1981 | Nelson | 128/136 |
| 4,351,331 | 9/1982 | Gereg | 128/DIG. 26 |

Primary Examiner—Stephen C. Pellegrino
Assistant Examiner—Mark Rooney
Attorney, Agent, or Firm—Kenneth R. Bowers, Jr.

[57] ABSTRACT

An interoral tube securing device which attaches to human teeth.

3 Claims, 4 Drawing Figures

INTERORAL TUBE FIXING DEVICE

BACKGROUND

This invention relates to fixtures for supporting a tube entering a human oral cavity.

For a variety of medical reasons, it is often desirable to insert a tube into a human oral cavity for extended intervals. The inserted tube should be fixed in position to prevent undesirable insertion or withdrawal of the tube. Presently, it is common practice to fix the tube by extensive taping of the tube to the external cheek and lips. This method is unsatisfactory because the tube is only weakly fixed, the tape is unsightly and uncomfortable, and may cause pain when removed.

Consequently it is desired to provide a device to secure an interoral tube.

SUMMARY

A disposable interoral securing device which anchors an interoral tube to natural teeth.

DETAILED DESCRIPTION

The invented tube securing device is designed for insertion within the oral cavity between the teeth and outer lip. The device is attached to the teeth using a cord which is passed between teeth through the gap therebetween in the manner commonly employed with dental floss. The cord size is suitable to produce a degree of jamming in the gap to enhance mechanical support. The device may be attached to either upper or lower teeth but attachment to upper jaw teeth is preferred.

The device may also serve as a bit block to prevent the crushing of the tube by the teeth.

Figure 1:
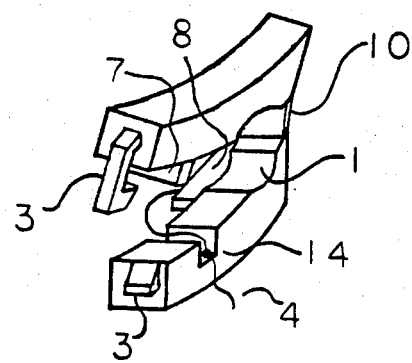
FIG. 1 is an isometric of an interoral securing device.
Figure 2:
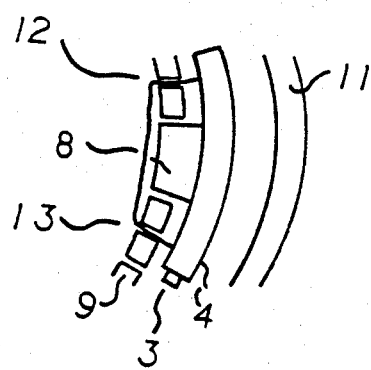
FIG. 2 is a plan schematic.

Refer to FIGS. 1-4 which illustrate a preferred embodiment. In FIG. 1, an uninstalled device is illustrated. A passage 1 is sized to secure and hold a tube 2 (in FIG. 4) when the device is closed. Closure of the device is maintained by a snap 3. A cord 4 is fixed at an end 5 (FIG. 4) and is passed through a slot 6. Closure of the device causes a block 7 to engage slot 6, crimping on cord 4 and holding cord 4 tightly. Passage 1 is surrounded by a bite block 8 which extends over teeth 9 as shown in FIG. 2.

It is intended that the entire device be made of a pliable, flexible material such as plastic or rubber, and be sufficiently inexpensive as to be disposable. The device may be an integral whole if sufficiently flexible to allow bending at joint 10.

The device should be thin to minimize discomfort and may be slightly curved as shown in FIGS. 1 and 2 to approximately match the shape of the mouth.

The device will be better understood by the steps followed during installation.

Figure 3:
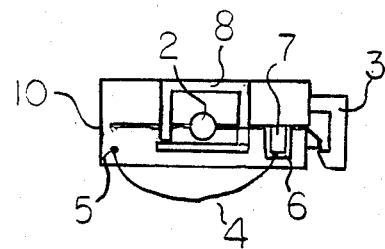
FIG. 3 is a profile schematic of an installed device.
Figure 4:
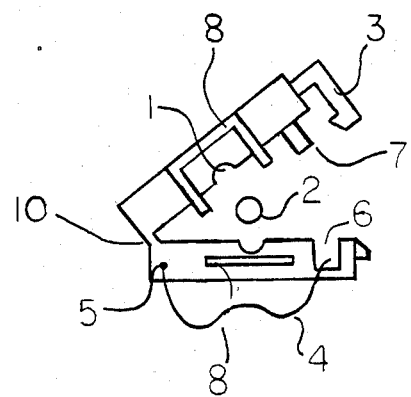
FIG. 4 is a profile schematic of a non-installed device.

With a tube 2 (FIG. 4) inserted the desired amount into the oral cavity, a device is inserted between lips 11 and teeth 9, such that tube 2 is within passage 1 and cord 4 passes through a first gap 12 (FIG. 2) between teeth 9. Cord 4 has sufficient length to enable passage behind several teeth 9, passage through a second gap 13, and passage through slot 6. Knots 14 (FIG. 1) may be tied in cord 4 in such position as to be located within slot 6 when cord 4 is drawn up to securely hold the device against the line of teeth 9. These knots 14 enhance the grip of block 7 on cord 4 when the device is closed. Block 7 and slot 6 may have a spherical recess (not shown) to receive such a knot 14. With tension held in cord 4, the device is closed, engaging snap 3 as shown in FIG. 3. This causes tube 2 to be held within slot 6. Also, tube 2 is protected by bite block 8. Cord 4 is somewhat jammed within gaps 12 and 13.

The unused portion of cord 4 may be cut and discarded.

Removal of the device may be done by cutting cord 4, opening snap 3, or by forcing cord 4 out of gaps 12 and 13.

I claim:

1. An interoral tube securing device having:
   (a) a body having a passage therethrough, said passage being sized to securely hold said tube;
   (b) a flexible cord attached at a first end to said body, adapted to pass through gaps between human teeth; and
   (c) attachment means on said body for capture of and securing to a second end of said cord;
   wherein said body has a first portion having a semicircular passage, said first portion attached to a second portion of said body and rotatable with respect thereto so as to bring the semicircular passage in said first portion in juxtaposition with a semicircular passage in said second portion thereby creating a passage adapted to secure a tube passed through said passage, and said second portion has a slot therethrough, and said first portion has a block adapted to mate with said slot thereby securing an end of said cord.

2. A process for securing an interoral tube securing device within an oral cavity which comprises:
   (a) locating the tube securing device in the oral cavity;
   (b) passing a flexible cord through a gap between two teeth; and
   (c) capturing said cord with attachment means on said tube securing device thereby securing said tube securing device within said oral cavity.

3. The process of claim 2 further comprising jamming said cord in said gap, said cord being of a diameter adapted to cause said cord to jam within said gap.

* * * * *